United States Patent [19]

Telschow et al.

[11] Patent Number: 4,560,772
[45] Date of Patent: Dec. 24, 1985

[54] PREPARATION OF SUBSTITUTED PHTHALIC ANHYDRIDES

[75] Inventors: Jeffrey E. Telschow, Tarrytown; Edward D. Weil, Hastings-on-Hudson, both of N.Y.

[73] Assignee: Stauffer Chemical Company, Westport, Conn.

[21] Appl. No.: 663,299

[22] Filed: Oct. 22, 1984

[51] Int. Cl.$^4$ ............................................. C07D 307/89
[52] U.S. Cl. ........................................ 549/240; 549/54
[58] Field of Search ................................. 549/240, 54

[56] References Cited

U.S. PATENT DOCUMENTS

| | | | |
|---|---|---|---|
| 2,264,429 | 12/1941 | Bergmann et al. | 549/240 |
| 2,391,226 | 12/1945 | Clifford et al. | 549/240 |
| 4,302,396 | 11/1981 | Tsujimoto et al. | 549/240 X |

FOREIGN PATENT DOCUMENTS 130638  11/1978  Japan .

OTHER PUBLICATIONS

Newman et al, JACS, vol. 63 (1941) pp. 1542-1544.
Craig, JACS, vol. 72 (1950) pp. 3732-3733.
Izv. Akad. Nauk. SSSR, Ser. Khim., 6 (1973) p. 1315, English translation, p. 1271.

*Primary Examiner*—Richard L. Raymond
*Attorney, Agent, or Firm*—Hensley M. Flash

[57] ABSTRACT

A process for preparing substituted phthalic anhydrides, example 4-methylphthalic, in which the Diels-Alder addition product of a conjugated diene, example isoprene, and maleic anhydride is reacted with sulfur in the presence of a catalyst. The catalyst is zinc oxide and 2-mercaptobenzothiazole. This reaction is carried out at elevated temperatures. A resulting thio derivative by-product can further be reacted with water at elevated temperatures in the presence of catalytic amounts of a base to form 4-methylphthalic anhydride. This base can be sodium hydroxide or N,N,N', N'-tetramethylguanidine. o-Dichlorobenzene can be added to prevent solids distillation during the process.

31 Claims, No Drawings

PREPARATION OF SUBSTITUTED PHTHALIC ANHYDRIDES

BACKGROUND OF THE INVENTION

1. Field of the Invention

This invention relates to a process for preparing substituted phthalic anhydrides. More particularly, it relates to a process for preparing 4-methylphthalic anhydride.

2. Related Art

Phthalic anhydrides are valuable raw materials for making various useful products. These anhydrides are useful as intermediates in the chemical synthesis of herbicides and particularly in the synthesis of certain herbicides used to protect cereal crops. Other uses for these raw materials include polycyclic dyes, alkyd and epoxy resins, polyesters and plasticizers.

Various processes are known for preparing substituted phthalic anhydrides. In two such processes 4-methyl-1,2,3,6-tetrahydrophthalic anhydride is dehydrogenated either by sulfur or by bromine in acetic acid. Yields of 4-methylphthalic anhydride of 59 percent to 87 percent are claimed for the former method, while the latter gives only a 16 percent yield [see Izv. Akad. Nauk. SSSR, Ser. Khim., 6, 1315 (1973) English translation, page 1271 and D. Craig, *Journal of American Chemical Society*, Vol. 72, page 3732, (1950)].

U.S. Pat. No. 2,391,226 (Clifford et al., Dec. 18, 1945) discloses addition products of chlormaleic anhydride and dichlormaleic anhydride prepared by the Diels-Alder reaction and the dehydrochlorination of these products in the presence of a catalyst, such as a secondary or tertiary amine. However, the six carbon ring is usually only partially dehydrogenated yielding a substituted dihydrophthalic anhydride.

U.S. Pat. No. 2,264,429 (Bergman, Dec. 2, 1941) discloses a process for preparing substituted phthalic anhydride in a single reaction. This reaction involves the combination of the condensation reaction between a diene and maleic anhydride and the dehydrogenation reaction. This combination is achieved by carrying out the condensation reaction in nitrobenzene or another nitrated aromatic substance, which not only acts as a diluent, but also as a dehydrogenating agent by reducing itself and giving the corresponding amine.

U.S. Pat. No. 4,302,396 (Tsujimoto et al., Nov. 24, 1981) discloses the preparation of 4-methylphthalic anhydride by the dehydrogenation of tetrahydro-4-methylphthalic anhydride with sulfur.

SUMMARY OF THE INVENTION

A process for preparing substituted phthalic anhydrides in good yield would be advantageous because of the various useful products that are prepared from these anhydrides. It is an object of the present invention to provide a unique, cost-effective process for the preparation of substituted phthalic anhydrides and, in particular, 4-methylphthalic anhydride. Other objects and advantages of the present invention are shown throughout the specification.

In accordance with the present invention, it has now been discovered that substituted phthalic anhydrides can be prepared by a process which comprises reacting the DielsAlder addition product of a conjugated diene and maleic anhydride with sulfur in the presence of a catalyst. The resulting thio derivative by-product can be further reacted with water to form more substituted phthalic anhydrides.

DETAILED DESCRIPTION OF THE INVENTION

The substituted phthalic anhydrides prepared by the processes of this invention can include a substituent or the lack of a substituent at each of the four available sites on the benzene ring, that is the 3, 4, 5 and 6 carbon positions. These substituents can be selected from the group consisting of $C_1$ to $C_{10}$ alkyl, $C_6$ to $C_{14}$ aryl and $C_1$ to $C_{16}$ aralkyl and wherein the alkyl, aryl and aralkyl substituents are optionally substituted with one or more halogen, cyano and/or carboxylic groups.

The process can use the Diels-Alder addition product as a starting material or can comprise a first step of actually preparing this addition product. The Diels-Alder addition product can be derived from other than the Diels-Alder reaction. In addition, the double bond isomers of the Diels-Alder addition product can be used in the process of this invention.

The Diels-Alder addition products of this invention are formed by reacting maleic anhydride with a conjugated diene. The conjugated diene can include butadiene, 2,3-dimethylbutadiene, other substituted butadienes and preferably isoprene.

The addition product can be prepared by reacting the maleic anhydride with the conjugated diene in a nitrogen atmosphere. The maleic anhydride is usually heated until it melts, then the conjugated diene is added slowly under the surface of the melt. When the addition of the diene is completed, the reactants can then be heated to a reaction temperature of from about 55° C. up to about 120° C. with temperatures in the upper end of the range from about 100° C. up to about 120° C. being preferred. The reactants are kept within the reaction temperature range until the reaction is completed, usually for about one hour. The reaction can be exothermic, therefore external cooling can be required to maintain the reactants within the reaction temperature range.

The stoichiometry of this Diels-Alder addition reaction usually involves one mole of the maleic anhydride reacting with one mole of the conjugated diene to produce one mole of the addition product, therefore it is economically desirable to react equimolar quantities of the reactants. However, a fractional molar excess of the diene is usually used to ensure that all the maleic anhydride is consumed in the reaction.

After the reaction to form the addition product is completed, excess diene can be stripped from the reaction zone under vacuum at a pressure which minimizes sublimation of the addition product and distillation of the solvent, if any is present.

The reaction used to prepare the addition product can take place in the presence or absence of an appropriate solvent. Such a solvent can be, for example, dimethylformamide, or any of the other solvents disclosed in the literature.

The reaction of the addition product with sulfur in the presence of a catalyst can be carried out directly upon the addition product/solvent solution after the excess diene is stripped from the reaction zone. The usual mode of addition is to add the catalyst first then add molten sulfur slowly over a period of time.

The stoichiometry of this reaction usually involves one mole of the Diels-Alder addition product reacting with two moles of sulfur to produce one mole of the phthalic anhydride, therefore it is economically desirable to react quantities of the reactants in as close to stoichiometric ratio as possible. However, a fractional molar excess of sulfur is usually used to ensure that all the Diels-Alder addition product is consumed in the reaction.

The catalyst used is a combination of zinc oxide and 2-mercaptobenzothiazole. Equal concentrations of each constituent of the catalyst combination is usually used. The concentration of each constituent of the catalyst combination used in this reaction can range from about 1 gram per 200 grams of Diels-Alder addition product to about 1 gram per 100 grams of Diels-Alder addition product.

The reaction of the Diels-Alder addition product with sulfur in the presence of a catalyst can take place at elevated temperature ranging from about 150° C. to about 250° C. with a preferred range of from about 190° C. to about 220° C. When isoprene is reacted with maleic anhydride, 4-methyl-1,2,3,6-tetrahydrophthalic anhydride is the resulting Diels-Alder addition product which can then be reacted with sulfur in the presence of a catalyst to prepare 4-methylphthalic anhydride.

When the Diels-Alder addition product is reacted with sulfur in the presence of a catalyst to prepare a substituted phthalic anhydride, a thio derivative also results. This thio derivative is a substituted phthalic thioanhydride which can further be reacted with water to form more substituted phthalic anhydride, enhancing the yield of the total process.

This reaction of the thio derivative with water can be carried out at elevated temperatures ranging from about 100° C. to about 250° C. with a preferred range from about 150° C. to about 180° C. Additionally, this reaction can be carried out in the presence of a catalytic amount of a base. Suitable bases can include sodium hydroxide and N,N,N',N'-tetramethylguanidine. The concentration of base used to catalyze this reaction can range from about 0.1 grams of base per 100 grams of crude phthalic anhydride to about 20 grams per 100 grams.

In the reaction of the thio derivative with water, oxygen is substituted for sulfur and a substituted phthalic anhydride results with the liberation of hydrogen sulfide gas.

A preferred processing mode includes adding catalytic amounts of base directly to the reaction mixture containing the thio derivative then adding water slowly while maintaining the mixture within the elevated temperature range disclosed above. Excess amount of water is used to obtain as great a conversion of thio derivative to the phthalic anhydride as possible.

During the many steps of the processes disclosed in this invention, solids distillation from the reaction zone can occur. Small quantities of orthodichlorobenzene can be added to the reaction to prevent solids distillation and the resulting solids deposits in the condenser.

In a preferred mode of the process of this invention, 4-methylphthalic anhydride is prepared. This preparation comprises reacting isoprene and maleic anhydride to form 4-methyl-1,2,3,6-tetrahydrophthalic anhydride, then reacting this product with sulfur in the presence of a catalyst comprising zinc oxide and 2-mercaptobenzothiazole at elevated temperatures ranging from about 190° C. to about 220° C. to form 4-methylphthalic anhydride and the thio derivative. The thio derivative can then be further reacted with water at elevated temperatures ranging from about 150° C. to about 180° C. in the presence of a base in catalytic amounts, such base being selected from the group consisting of sodium hydroxide and N,N,N',N'-tetramethylguanidine, and in the presence of orthodichlorobenzene to form further quantities of 4-methylphthalic anhydride. In another preferred embodiment 4-methylphthalic anhydride can be prepared by a process which comprises a first step of reacting the Diels-Alder addition product with sulfur in the presence of a catalyst, then proceeding to further react the resulting thio derivative to form further quantities of the desired end product.

The following example describes various embodiments of the invention. Other embodiments will be apparent to the skilled in the art from a consideration of this specification or practice of the invention disclosed herein. It is intended that the specifications and example be considered as exemplary only with the true scope and spirit of the invention being indicated by the claims which follow the example.

EXAMPLE

In a 1 liter 3-necked flask fitted with a dropping funnel, a mechanical stirrer, a pot thermometer and a condenser was placed 98.1 grams (1.0 mole) of maleic anhydride. The flask was heated in an oil bath until the maleic anhydride melted. Isoprene (69.5 grams, 1.02 moles) was then added dropwise to the flask below the surface of the maleic anhydride melt, using an extension tube of TEFLON fluorocarbon polymer attached to the dropping funnel, at such a rate as to minimize the reflux. The temperature of the reactants in the flask was controlled with intermittent cooling and kept between 55° and 100° C.

After the addition of the isoprene was completed, the reactor flask was heated to 120° C. and maintained at that temperature for 60 minutes to ensure complete reaction. Excess isoprene was then stripped from the reactor at 10-50 mm/90° C. for 20 minutes.

The faintly yellow, molten 4-methyl-1,2,3,6-tetrahydrophthalic anhydride (4-MTPA, mp 58°-63° C.) was formed in the reactor flask.

To the molten 4-MTPA was added 1 gram each of zinc oxide and 2-mercaptobenzothiazole (catalyst) and 25 milliliters of o-dichlorobenzene (bp 178° C.). The o-dichlorobenzene was added to prevent solid deposits in the condenser.

This mixture was heated to 220° C. and treated dropwise with molten sulfur (67.4 grams, 2.1 moles) over a 2 hour period. The liberated $H_2S$ was trapped in caustic solution. After an additional 30 minutes of heating at 220° C., no more gas evolution was observed. The mixture was cooled to below 100° C. and G.C. analysis indicated about 17 area percent of 4-methylphthalic thioanhydride.

Two grams of 50 percent sodium hydroxide was added to the reaction mixture which was maintained at 170°-180° C. as water was added slowly via syringe pump. The thioanhydride was thus converted to the desired anhydride with the liberation of $H_2S$. Unreacted water was allowed to reflux until temperature control became difficult, then water was allowed to distill. A total of 9 milliliters of water was added over about 5 hours. At the end of this time, G.C. analysis indicated about 2 area percent of the thioanhydride remaining. Vacuum distillation gave 103.7 grams (64 percent yield) of yellow solids, boiling point 142°-143° C./6 millimeters and about 93 area percent pure by G.C. analysis.

What is claimed is:

1. A process for preparing a substituted phthalic anhydride which comprises reacting the Diels-Alder addition product of a conjugated diene and maleic anhydride with sulfur in the presence of zinc oxide and 2-mercaptobenzothiazole as a catalyst.

2. The process of claim 1 wherein the reaction is carried out at elevated temperatures ranging from about 150° C. to about 250° C.

3. A process for preparing 4-methylphthalic anhydride which comprises reacting 4-methyl-1,2,3,6-tetrahydrophthalic anhydride with sulfur in the presence of zinc oxide and 2-mercaptobenzothiazole as a catalyst.

4. The process of claim 5 wherein the reaction is carried out at elevated temperatures ranging from about 150° C. to about 250° C.

5. A process for preparing a substituted phthalic anhydride which comprises:
   (a) reacting a conjugated diene and maleic anhydride to form a Diels-Alder addition product;
   (b) reacting the addition product with sulfur in the presence of zinc oxide and 2-mercaptobenzothiazole as a catalyst.

6. The process of claim 5 wherein reaction step (b) is carried out at elevated temperatures ranging from about 150° C. to about 250° C.

7. A process for preparing 4-methylphthalic anhydride which comprises:
   (a) reacting isoprene and maleic anhydride to form 4-methyl-1,2,3,6-tetrahydrophthalic anhydride;
   (b) reacting the 4-methyl-1,2,3,6-tetrahydrophthalic anhydride with sulfur in the presence of zinc oxide and 2-mercaptobenzothiazole as a catalyst.

8. The process of claim 7 wherein reaction step (b) is carried out at elevated temperatures ranging from about 150° C. to about 250° C.

9. A process for preparing a substituted phthalic anhydride which comprises:
   (a) reacting the Diels-Alder addition product of a conjugated diene and maleic anhydride with sulfur in the presence of zinc oxide and 2-mercaptobenzothiazole as a catalyst to form the substituted phthalic anhydride and a thio derivative;
   (b) further reacting the thio derivative with water to form a substituted phthalic anhydride.

10. The process of claim 9 wherein reaction step (a) is carried out at elevated temperatures ranging from about 150° C. to about 250° C.

11. The process of claim 9 wherein said conjugated diene is isoprene.

12. The process of claim 9 wherein reaction steo (b) is carried out at elevated temperatures ranging from about 100° C. to about 250° C.

13. The process of claim 9 wherein reaction step (b) is carried out in the presence of a catalytic amount of a base.

14. The process of claim 13 wherein the base is sodium hydroxide.

15. The process of claim 13 wherein the base is N,N,N',N'-tetramethylguanidine.

16. The process of claim 13 wherein reaction step (b) is carried out in the presence of o-dichlorobenzene.

17. A process for preparing a substituted phthalic anhydride which comprises:
   (a) reacting a conjugated diene and maleic anhydride to form a Diels-Alder addition product;
   (b) reacting the addition product with sulfur in the presence of zinc oxide and 2-mercaptobenzothiazole as a catalyst to form a substituted phthalic anhydride and a thio derivative;
   (c) further reacting the thio derivative with water to form the substituted phthalic anhydride.

18. The process of claim 17 wherein reaction step (b) is carried out at elevated temperatures ranging from about 150° C. to about 250° C.

19. The process of claim 17 wherein reaction step (c) is carried out at elevated temperatures ranging from about 100° C. to about 250° C.

20. The process of claim 17 wherein reaction step (c) is carried out in the presence of a catalytic amount of a base.

21. The process of claim 20 wherein the base is sodium hydroxide.

22. The process of claim 20 wherein the base is N,N,N',N'-tetramethylguanidine.

23. The process of claim 20 wherein reaction step (c) is carried out in the presence of o-dichlorobenzene.

24. A process for preparing 4-methylphthalic anhydride which comprises:
   (a) reacting isoprene and maleic anhydride to form 4-methyl-1,2,3,6-tetrahydrophthalic anhydride;
   (b) reacting the 4-methyl-1,2,3,6-tetrahydrophthalic anhydride with sulfur in the presence of zinc oxide and 2-mercaptobenzothizole as a catalyst to form 4-methylphthalic anhydride and a thio derivative;
   (c) further reacting the thio derivative with water to form 4-methylphthalic anhydride.

25. The process of claim 24 wherein the reaction step b) is carried out at elevated temperatures ranging from about 150° C. to about 250° C.

26. The process of claim 24 wherein reaction step (c) is carried out at elevated temperatures ranging from about 100° C. to about 250° C.

27. The process of claim 24 wherein reaction step (c) is carried out in the presence of catalytic amounts of a base.

28. The process of claim 27 wherein the base is sodium hydroxide.

29. The process of claim 27 wherein the base is N,N,N',N'-tetramethylguanidine.

30. The process of claim 27 wherein reaction step (c) is carried out in the presence of o-dichlorobenzene.

31. The process for preparing 4-methylphthalic anhydride which comprises:
   (a) reacting isoprene and maleic anhydride to form 4-methyl-1,2,3,6-tetrahydrophthalic anhydride;
   (b) reacting the 4-methyl-1,2,3,6-tetrahydrophthalic anhydride with sulfur in the presence of a catalyst comprising zinc oxide and 2-mercaptobenzothiazole at elevated temperatures ranging from about 190° C. to about 220° C. to form 4-methylphthalic anhydride and a thio derivative;
   (c) further reacting the thio derivative with water at elevated temperatures ranging from about 150° C. to about 180° C. in the presence of a base in catalytic amounts, such base being selected from the group consisting of sodium hydroxide and N,N,N',N'-tetramethylguanidine, and in the presence of o-dichlorobenzene to form 4-methylphthalic anhydride.

* * * * *

UNITED STATES PATENT AND TRADEMARK OFFICE
CERTIFICATE OF CORRECTION

PATENT NO. : 4,560,772
DATED : December 24, 1985
INVENTOR(S) : Jeffrey E. Telschow et al.

It is certified that error appears in the above—identified patent and that said Letters Patent is hereby corrected as shown below:

Col. 1, line 66, change "DielsAlder" to "Diels-Alder";

Claim 4, first line, change "claim 5" to "claim 3";

Claim 12, first line, change "steo" to "step"; and

Claim 24, (b), third line, change "2-mercaptobenzothizole" to "2-mercaptobenzothiazole.

Signed and Sealed this

First Day of April 1986

[SEAL]

Attest:

DONALD J. QUIGG

Attesting Officer

Commissioner of Patents and Trademarks